United States Patent [19]
Bock et al.

[11] Patent Number: 5,206,238
[45] Date of Patent: Apr. 27, 1993

[54] CHOLECYSTOKININ ANTAGONISTS

[75] Inventors: Mark G. Bock, Hatfield; Roger M. Freidinger, Lansdale, both of Pa.

[73] Assignee: Merck & Co., Inc., Rahway, N.J.

[21] Appl. No.: 870,157

[22] Filed: Apr. 15, 1992

Related U.S. Application Data

[63] Continuation of Ser. No. 612,646, Nov. 13, 1990, abandoned.

[51] Int. Cl.$^5$ .............................................. A01K 31/55
[52] U.S. Cl. ...................................................... 514/221
[58] Field of Search ........................................ 514/221

[56] References Cited

U.S. PATENT DOCUMENTS

| | | |
|---|---|---|
| 4,628,084 | 12/1986 | Bock et al. |
| 4,684,646 | 8/1987 | Chang et al. ............... 514/221 |
| 4,724,237 | 2/1988 | Bock et al. ................. 514/221 |
| 4,798,826 | 1/1989 | Peck ........................... 514/221 |
| 4,820,834 | 4/1989 | Evans et al. ................. 514/221 |
| 4,873,076 | 10/1989 | Fishman et al. ............. 424/10 |
| 4,929,614 | 5/1990 | Calvet et al. ................ 514/214 |
| 4,957,915 | 9/1990 | Kim et al. ................... 514/221 |
| 4,970,207 | 11/1990 | Sato et al. ................... 514/211 |

FOREIGN PATENT DOCUMENTS

| | | |
|---|---|---|
| 0304223 | 2/1989 | European Pat. Off. |
| 411668 | 2/1991 | European Pat. Off. |

OTHER PUBLICATIONS

Bradwejn, et al., *Enhanced Sensitivity to Cholecystokinin Tetrapeptide in Panic Disorder*, Soc. Neurosci. Abstr. 14(1), p. 291, (1988).
de Montigny, *Cholecystokinin Tetrapeptide Induces Panic Attacks in Healthy Volunteers*, Soc. Neurosci. Abstr. 14(1), p. 291, (1988).
Bradwejn, et al., *Benzodiazepines Antagonize Cholecystokinin—Induced Activation of Rat Hippocampal Neurones*, Nature 312, p. 22, (1984).
de Montigny, *Cholecystokinin Tetrapeptide Induces Panic-like Attacks in Healthy Volunteers*, Arch. Gen. Psychiatry, 46, pp. 511–517, (1989).
Dourish, et al., *Enhancement of Morphine Analgesia and Prevention of Morphine Tolerance in the Rat by the Cholecystokinin Antagonist L-364,718*, Pharm. 147, pp. 469–472, (1988).
Bouthillier, et al.,*Long-term Benzodiazepine Treatment Reduces Neuronal Responsiveness to Cholecystokinin: An Electrophysiological Study in the Rat*, Eur. Jour. Pharm. 151, No. 1, pp. 135–138, (1988).
O'Neill et al. *Morhpine Induced Analgesia in the Rat Paw Pressure Test is Blocked by CCK and Enhanced by the CCK Antagonist MK-329*, Neuropharmacology 28, No. 3, pp. 243–247 (1989).
Chang, et al., *Biochemical and Pharmacological Characterization of an Extremely Potent and Selective Nonpeptide Cholecystokinin Antagonist*, Proc. Natl. Acad. Sci., 83, pp. 4923–4926 (1986).
Bock, et al., *Benzodiazepine Gastrin and Brain Cholecystokinin Receptor Ligands: L-365,260*, Journal of Medicinal Chemistry, 32, No. 1, pp. 13–16 (1989).

*Primary Examiner*—S. J. Friedman
*Attorney, Agent, or Firm*—Francis P. Bigley; Joseph F. DiPrima

[57] ABSTRACT

Compounds of the formula:

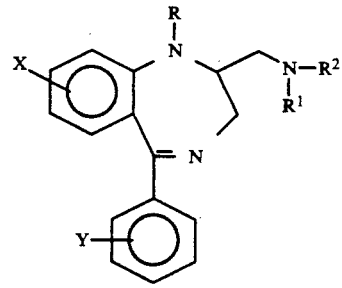

are disclosed which are antagonists of gastrin and cholecystokinin (CCK) and have properties useful for treating panic disorder and for directly inducing anlagesia.

6 Claims, No Drawings

CHOLECYSTOKININ ANTAGONISTS

This is a continuation of application Ser. No. 07/612,646 filed Nov. 13, 1990, now abandoned.

CROSS-REFERENCE

Starting materials for the compounds of this invention are prepared and described in U.S. Pat. No. 4,724,237, which is incorporated herein by reference.

FIELD OF THE INVENTION

This invention relates to the discovery of compounds for use as antagonists of cholecystokin (CCK) and gastrin when administered to animals, preferably humans.

BACKGROUND OF THE INVENTION

The compounds of this invention are useful in treating various diseases caused by an excess of CKK or gastrin. Cholecystokinins (CCK) and gastrin are structurally related neuropeptides which exist in gastrointestinal tissue and in the central nervous system (see, V. Mutt, *Gastrointestinal Hormones*, G. B. J. Glass, Ed., Raven Press, N.Y., p. 169 and G. Nission, ibid. p. 127.

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-NH$_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, *Biomed. Res.* 3 107 [1982]; and J. E. Morley, *Life Sci.* 30, 479, [1982]).

The primary role of gastrin, on the other hand, appears to be stimulation of the secretion of water and electrolytes from the stomach, and, as such, it is involved in control of gastric acid and pepsin secretion. Other physiological effects of gastrin then include increased mucosal blood flow and increased antral motility, with rat studies having shown that gastrin has a positive trophic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, preferably mammals, and especially those of humans. Just as there is some overlap in the biological activities of CCK and gastrin, antagonists also tend to have affinity for both receptors. In a practical sense, however, there is enough selectivity for the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., *Science* 226, 1215 (1984)]. Selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value. See e.g. U.S. Pat. No. 4,820,834. It is further expected that the CCK antagonists of Formula I are useful anxiolytic agents particularly in the treatment of panic disorder.

Since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202,303 (1985)].

Four distinct chemical classes of CCK-receptor antagonists have been reported [R. Freidinger, *Med. Res. Rev.* 9, 271 (1989)]. The first class comprises derivatives of cyclic nucleotides, of which dibutyryl cyclic GMP has been shown to be the most potent by detailed structure-function studies (see, N. Barlas et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-NH$_2$, Met-Asp-Phe-NH$_2$), and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

The third class of CCK-receptor antagonists comprises the amino acid derivatives: proglumide, a derivative of glutamic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Biophys. Acta.*, 761, 269 (1983)]. All of these compounds, however, are relatively weak antagonists of CCK (IC$_{50}$: generally $10^{-4}$M[although more potent analogs of proglumide have been recently reported in F. Makovec et al., *Arzneim-Forsch Drug Res.*, 35 (II), 1048 (1985) and in German Patent Application DE 3522506A1], but down to $10^{-6}$M in the case of peptides), and the peptide CCK-antagonists have substantial stability and absorption problems.

A fourth class of compounds consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications 167 919, 167 920 and 169 392, B. E. Evans et al, *Proc. Natl. Acad. Sci. U.S.A.*, 83, p. 4918–4922 (1986) and R.S.L. Chang et al., ibid, p. 4923–4926] have also been reported.

No really effective receptor antagonists of the in vivo effects of gastrin have been reported (J. S. Morley, *Gut Pept. Ulcer Proc.*, Hiroshima Symp. 2nd, 1983, p. 1), and very weak in vitro antagonists, such as proglumide and certain peptides have been described [(J. Martinez, *J. Med. Chem.* 27, 1597 (1984)]. Recently, however, pseudopeptide analogs of tetragastrin have been reported to be more effective gastrin antagonists than previous agents [J. Martinez et al., *J. Med. Chem.*, 28, 1874-1879 (1985)].

It is, therefore, an object of this invention to identify substances which more effectively antagonize or inhibit the function of cholecystokinins and gastrin in psychiatric disease states ivolving anxiety or panic in animals, especially in humans. It is another object of this invention to develop a method of antagonizing the functions of cholecystokinin and/or gastrin in panic disorder or other neurological disorders involving anxiety or panic in animals, especially in humans. It is also an object of this invention to develop a method of preventing or treating neurochemical disorders involving panic disorder, panic syndrome and similar anxiety states.

The compounds of the present invention are also useful for directly inducing analgesia, which includes opiate and non-opiate mediated analgesia. Furthermore, the compounds of the present invention are useful as anesthetic agents involving the loss of pain sensation. It is therefore another object of the present invention to identify substances which more effectively antagonize or inhibit the function of CCK or gastrin for the purpose of effecting analgesia, anesthesia, or loss of pain sensation. Yet another object of the present invention is to develop methods of antagonizing or inhibiting the functions of CCK or gastrin for the purpose of effecting analgesia, anesthesia or loss of pain sensation.

SUMMARY OF THE INVENTION

The present invention provides compounds of the formula:

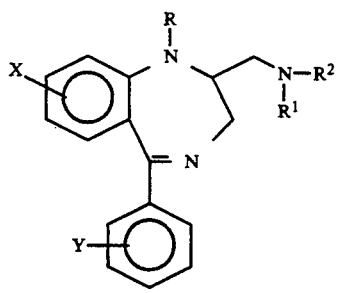

for use as antagonists of CCK and gastrin. The above-mentioned compounds can be used in a method of acting upon a CCK and/or gastrin receptor which comprises administering a therapeutically effective but non-toxic amount of such compound to an animal, especially a human. A pharmeutical composition comprising a pharmaceutically acceptable carrier and, dispersed therein, an effective but non-toxic amount of these compounds is useful in the treatment and prevention of CCK-related neurochemical disorders such as panic disorder, panic syndrome and similar anxiety states, and are also useful in effecting analgesia. Methods of treating such disorders and for effecting analgesia are also disclosed.

DETAILED DESCRIPTION OF THE INVENTION

The compounds of this invention are useful in a method of antagonizing the binding of CCK to CCK receptors or antagonizing the binding of gastrin to gastrin receptors, for treating panic disorder and for inducing analgesia, which comprises contacting the CCK receptors or the gastrin receptors, respectively, with compounds having the formula:

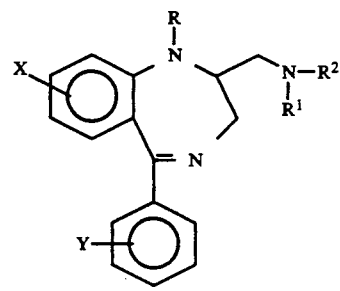

wherein:
X is one or two of the substituents: F, Cl or Br; $C_1$–$C_4$-straight- or branched-chain alkyl, including methyl, ethyl, propyl, isopropyl, butyl, isobutyl, and t-butyl; $C_1$–$C_4$-alkoxy; $C_1$–$C_4$-alkylthio; hydroxy; nitro; cyano; amino; or trifluoromethyl, and may be attached at either or both the 7- and/or 8-positions;

Y is independently, the same as X, and may be attached at any of positions 2–6 on the aromatic ring;

R is H, $C_1$–$C_4$-alkyl, cyclo-$C_3$–$C_5$-alkyl, $C_1$–$C_4$-alkenyl, or acetyl;

$R^1$ is H, $C_1$–$C_4$-alkyl, or cyclo-$C_3$–$C_5$-alkyl;

$R^2$ is unsubstituted or mono- or disubstituted phenyl, where the substituents are as defined under X, above;

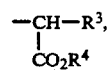

where $R^3$ is $(CH_2)_n$-$C_1$-$C_4$-alkyl, —$(CH_2)_n$-2-indole, —$(CH_2)_n$-3-indole, or —$(CH_2)_n$-phenyl (unsubstituted or mono- or disubstituted, where the substituents are as defined for X, above), where n is 0–4, and $R^4$ is H or $C_1$-$C_4$-alkyl;

where $R^5$ is

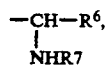

wherein $R^6$ is $(CH_2)_n$-2-indole, or $(CH_2)_n$-3-indole, where n is 0–4, where $R^7$ is H, $COOR^8$, or

and where $R^8$ is $C_1$–$C_4$-alkyl; where $R^5$ is $(CH_2)_mSCH_2NHCOCH_3$, where m is 1–4; where $R^5$ is $C_1$–$C_4$-alkyl; where $R^5$ is pyrazine (unsubstituted or mono-substituted where the substituents may be Cl, $COOR^8$, CN or $NO_2$), wherein $R^8$ is as defined above;
where $R^5$ is

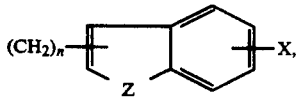

wherein Z is O, S or NR, $(CH_2)_n$ is attached at the 2- or 3-position, and R, n and X are as defined above;
where $R^5$ is

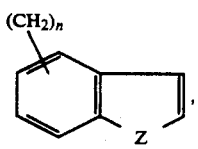

wherein $(CH_2)_n$ is attached at the 4- or 5-position, and n and Z are as defined above; where $R^5$ is $(CH_2)_mCO_2CH_2$phenyl, wherein m is as defined above;
where $R^5$ is —O—$C_1$–$C_4$-alkyl, —CHOH$C_6H_5$, or

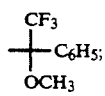

or of the formula II:

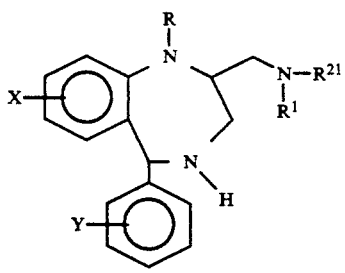

wherein:
X, Y, R and $R^1$ are as defined above; and $R^{21}$ is $R^2$ as defined above, including wherein $R^5$, as defined above, also is pyridine,

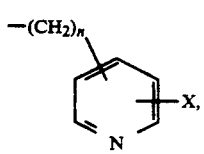

where $(CH_2)_n$ is attached at the 2-, 3- or 4-position and n and X are as defined above;

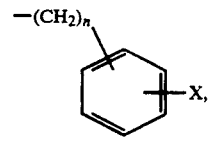

where the point of attachment is at any position on the ring and n and X are as defined above; or

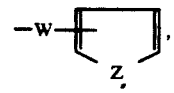

where the point of attachment is at the 2- or 3-position and W is H, straight or branched chain $C_1$–$C_4$-alkyl or $C_1$–$C_4$-alkoxy, nitro, F, Cl or Br, and Z is as defined above; or
the optical isomers of formula I, or pharmaceutically acceptable salts of the compounds of formulas I or II.
Preferred compounds of formula I according to the instant invention include those in which X is F or Cl; R is H or $C_1$–$C_4$-alkyl; $R^1$ is H; $R^2$ is

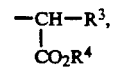

wherein $R^3$ is —$(CH_2)$-phenyl or $(CH_2)$-2 or 3-indole, and $R^4$ is $C_1$–$C_4$-alkyl; or $R^2$ is

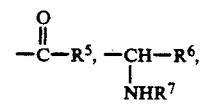

where $R^6$ is $(CH_2)$-2-indole or $(CH_2)$-3-indole and $R^7$ is H, $COOR^8$, or

wherein $R^8$ is $C_1$–$C_4$-alkyl; or $R^5$ is

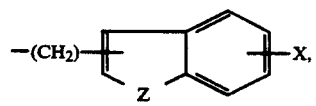

wherein Z is O, S or NR and X and R are as defined above; or $R^5$ is

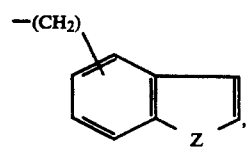

wherein Z is as defined above; or $R^5$ is —CHOH$C_6H_5$.
Preferred compounds of formula II according to the instant invention include those in which X is F or Cl; R is H or $C_1$–$C_4$-alkyl; $R^1$ is H; $R^2$ is

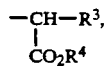

wherein R³ is —(CH₂)-phenyl or (CH₂)-2 or 3-indole, and R⁴ is C₁–C₄-alkyl; or R² is

wherein R⁵ is

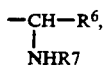

where R⁶ is (CH₂)-2-indole or (CH₂)-3-indole and R⁷ is H, COOR⁸, or

wherein R⁸ is C₁–C₄-alkyl; or R⁵ is

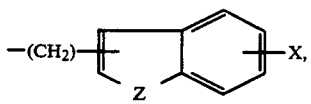

wherein Z is O, S or NR and X, R and n are as defined above; or R⁵ is

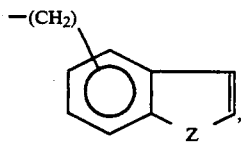

wherein Z is as defined above; or R⁵ is —CHOHC₆H₅; or R⁵ is

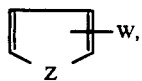

wherein W and Z are as defined above; R⁵ is

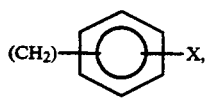

wherein X is as defined above.

Particularly preferred compounds of formula I include:

1-methyl-2-(2'-indolecarbonyl)aminomethyl-5-(2'-fluorophenyl)-2,3-dihydro-1H-1,4-benzodiazepine,
1-methyl-2-(4-thianaphthenemethylcarbonyl)aminomethyl-5-(2'-fluorophenyl)-2,3-dihydro-1H-1,4-benzodiazepine,
1-methyl-2-(2-L-hydroxy-2-phenylacetyl)aminomethyl-5-(-2'-fluorophenyl)-2,3-dihydro-1H-1,4-benzodiazepine,
1-methyl-2-(3'-trifluoromethylphenyl)aminomethyl-5-(2'-fluorophenyl)-2,3-dihydro-1H-1,4-benzodiazepine,
1-methyl-2-[1-(S)-1-methoxycarbonyl-2-phenylethylamino]methyl-5-(2'-fluorophenyl)-2,3-dihydro-1H-1,4-benzodiazepine,
1-methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine,
1-methyl-2-[(2-methylpropoxy)carbonyl]aminomethyl-5-(2'-fluorophenyl)-2,3-dihydro-1H-1,4-benzodiazepine,
1-methyl-2-[2-amino-3-(1H-indol-3-yl)propanoyl]aminomethyl-5-(2'-fluorophenyl)-2,3-dihydro-1H-1,4-benzodiazepine,
1-methyl-2-(2-methoxy-2-trifluoromethyl-2-phenylacetyl)aminomethyl-5-(2'-fluorophenyl)-2,3-dihydro-1H-1,4-benzodiazepine,
1-methyl-2-[2-(S)-((1,1-dimethylethoxy)carbonyl)amino-3-acetamidoethylmercaptopropanoyl]aminomethyl-5-(2'-fluorophenyl)-2,3-dihydro-1H-1,4-benzodiazepine,
1-methyl-2-benzylsuccinoylaminomethyl-5-(2'-fluorophenyl)-2,3-dihydro-1H-1,4-benzodiazepine, and
1-methyl-2-(acetamidomethylmercaptoacetyl)aminomethyl-5-(2'-fluorophenyl)-2,3-dihydro-1H-1,4-benzodiazepine.

Particularly preferred compounds of formula II include:

1-methyl-2-(2'-indolecarbonyl)aminomethyl-5-(2'-fluorophenyl)-2,3,4,5-tetrahydro-1H-1,4-benzodiazepine,
1-methyl-2-(4-thianaphthenemethylcarbonyl)aminomethyl-5-(2'-fluorophenyl)-2,3,4,5-tetrahydro-1H-1,4-benzodiazepine,
1-methyl-2-(2-L-hydroxy-2-phenylacetyl)aminomethyl-5-(2'-fluorophenyl)-2,3,4,5-tetrahydro-1H-1,4-benzodiazepine,
1methyl-2-(1H-indol-3-yl)methylcarbonylaminomethyl-5-(2'-fluorophenyl)-2,3,4,5-tetrahydro-1H-1,4-benzodiazepine,
1-methyl-2-(3-thiophenecarbonyl)aminomethyl-5-(2'-fluorophenyl)-2,3,4,5-tetrahydro-1H-1,4-benzodiazepine,
1-methyl-2-(4-chlorobenzoyl)aminomethyl-5-(2'-fluorophenyl)-2,3,4,5-tetrahydro-1H-1,4-benzodiazepine, and
1-methyl-2-o-fluorobenzoylaminomethyl-5-(2'-fluorophenyl)-2,3,4,5-tetrahydro-1H-1,4-benzodiazepine.

The most preferred compounds of this invention include the following:

1-methyl-2-(2'-indolecarbonyl)aminomethyl-5-(2'-fluorophenyl-2,3-dihydro-1H-1,4-benzodiazepine

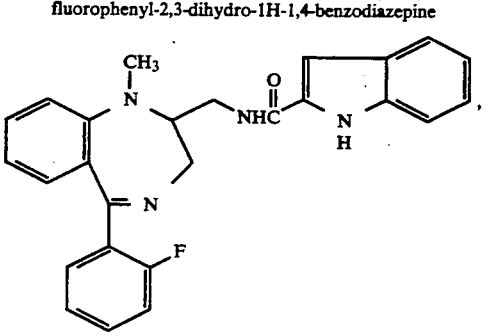

1-methyl-2-(4-thianaphthenemethylcarbonyl)aminomethyl-

-continued 5-(2'-fluorophenyl)-2,3-dihydro-1H-1,4-benzodiazepine

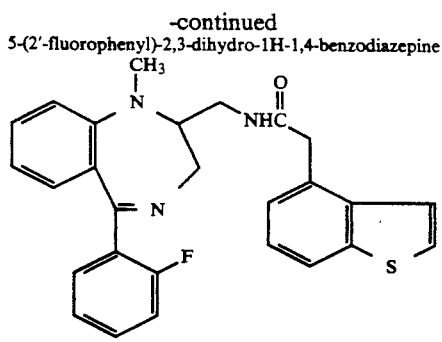

1-methyl-2-(4-chlorophenyl)aminomethyl-5-(2'-fluoro-phenyl)-2,3,4,5-tetrahydro-1H-1,4-benzodiazepine

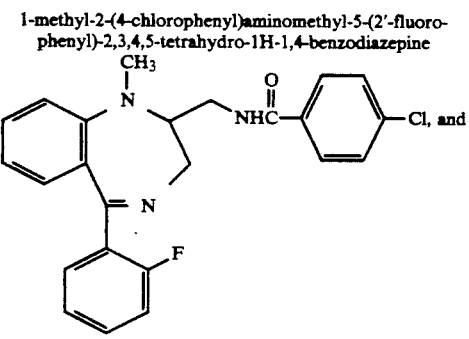

1-methyl-2-(2-L-hydroxy-2-phenylacetyl)aminomethyl-5-(2'-fluorophenyl)-2,3-dihydro-1H-1,4-benzodiazepine

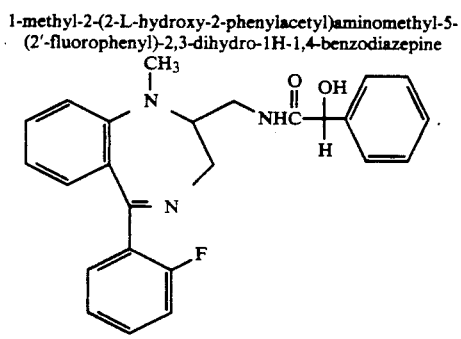

The pharmaceutically acceptable salts of the compounds of this invention include the conventional non-toxic salts or the quarternary ammonium salts of the compounds formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of this invention which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of this invention are also readily prepared by conventional procedures such as treating an acid of the compound of this invention with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of this invention antagonize CCK and/or gastrin and are useful as pharmaceutical agents for animals, preferably for mammals, and most especially for humans, for the treatment and prevention of disorders wherein CCK and/or gastrin may be involved. Examples of such disease states include gastrointestinal disorders especially irritable bowel syndrone, gastroesophagenal reflux disease, excess pancreatic or gastrin secretion, acute pancreatitis, or motility disorders; central nervous system disorders, caused by CCK interaction with dopamine, such as neusoleptic disorders, tardine dyskinesia, Parkinson's disease, psychosis or Gilles de la Tourette syndrome; disorders of appetite regulatory systems; Zollinger-Ellison syndrome, antral and cell hyperplasia, or pain (potentiation of opiate and gesin) as well as certain tumors of the lower esophagus, stomach, intestine, colon and lung, including small cell lung carcinoma.

The compounds of this invention may further be useful in the treatment or prevention of neurological disorders involving anxiety and other panic type states wherein CCK and/or gastrin is involved. Examples of such disorders include panic disorders, panic syndrome, anticipatory anxiety, phobic anxiety, panic anxiety, chronic anxiety, and endogenous anxiety. The compounds are also useful for directly inducing analgesia, opiade or non-opiade mediated, as well as anesthesia or loss of the sensation of pain.

The present invention also encompasses a pharmaceutical composition useful in the treatment of the CCK and/or gastrin disorders as set forth above, comprising the administration of a therapeutically effective but non-toxic amount of the compounds of Formula I, with or without pharmaceutically acceptable carriers or diluents.

The compounds of this invention may be administered to animals, preferably to mammals, and most especially to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to this invention is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 µg/kg to about 5 mg/kg of body weight, and preferably, of from about 0.5 µg/kg to about 0.5 mg/kg of body weight, administered in single or divided doses. In some cases, however, it may be necessary to use dosages outside these limits.

In the effective treatment of panic syndrome, panic disorder and the like, about 0.005 µg/kg to about 0.5 mg/kg of CCK antagonist is administered orally (p.o.), divided into two doses per day (b.i.d.). Other routes of administration are also suitable.

For directly inducing analgesia, anesthesia or loss of pain sensation, the effective dosage ranges from about 100 ng/kg to about 1 mg/kg by intraperitoneal administration. Oral administration is an alternative route, as well as others.

In the treatment of irritable bowel syndrome, about 0.1 to 10 mg/kg of CCK antagonist is administered orally (p.o.), divided into two dosages per day (b.i.d.). Other routes of administration are also suitable.

The use of a gastrin antagonist as a tumor palliatine for gastrointestinal neoplasma with gastrin receptors, as a modulator of central nervous activity, treatment of Zollinger-Ellison syndrome, or in the treatment of peptic ulcer disease, an effective dosage of about 0.1 to about 10 mg/kg administered one-to-four times daily is indicated.

Because these compounds antagonize the function of CCK in animals, they may also be used as feed additives to increase the food intake of animals in daily dosage of approximately 0.005 to 100 µg/kg of body weight.

The compounds of this invention are prepared according to the reaction schemes set forth in U.S. Pat. No. 4,724,237, incorporated herein by reference. An additional reaction scheme is set forth as follows:

SCHEME 1

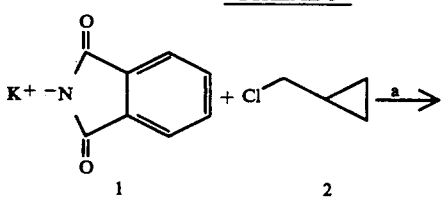

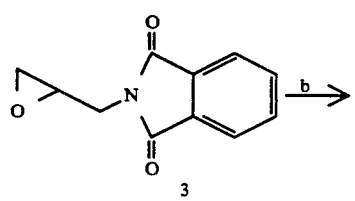

-continued
SCHEME 1

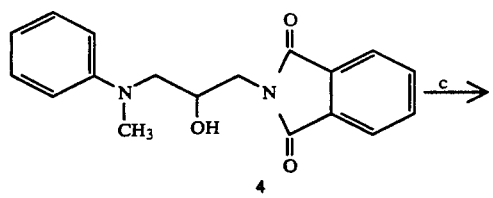

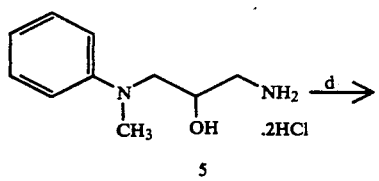

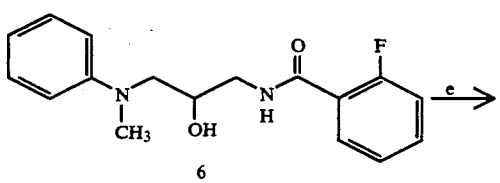

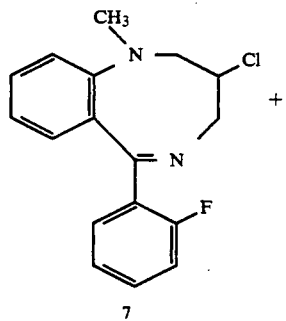

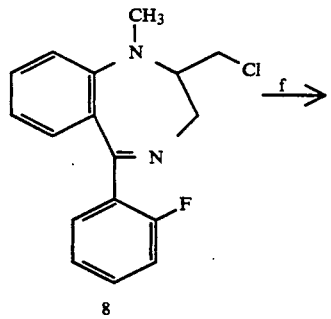

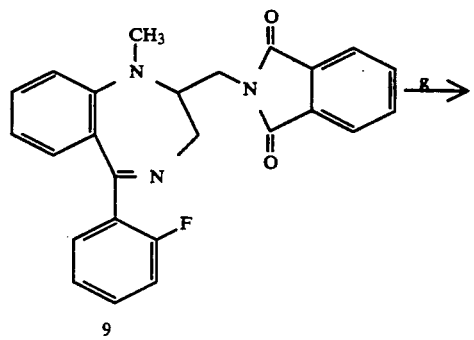

-continued
SCHEME 1

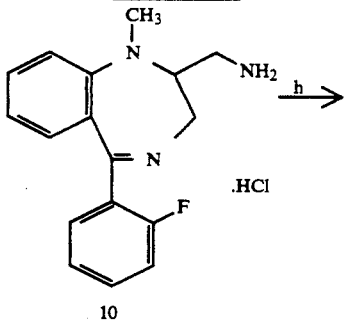

10

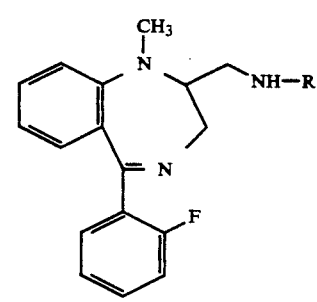

11

(a) 160°, 18 hr., E. Titus, J. Org. Chem., (1988), 13, 50.

Steps (b)⟶(g) according to W. Milkowsky, et al., Eur. J. Med. Chem., (1976) 11 (6), 501, incorporated herein by reference, and
(h) carboxylic acid, 1-ethyl-3-dimethylaminopropylcarbodiimide.HCl, methylene chloride, triethylamine.

MATERIALS AND METHODS

1. Anxiolytic Activity of the Compounds of Formula I

The black/white exploration test [Crawley et al. Pharmacology, Biochemistry and Behav. 13, 167 (1980)] is a simple animal model of anxiety. Rodents placed in a two compartment box which consists of a brightly lit, white painted side and a dimly lit, black painted side, display a marked preference for the black side of the apparatus. This behavior is caused by the aversive properties of the brightly lit, white painted section. Classical anxiolytic drugs [such as diazepam, see Crawley, supra] and novel anxiolytic drugs [such as $5HT_3$ antagonists, see Jones et al. Br. J. Pharm. 93, 985 (1988)] decrease the preference of the animal for the black dimly lit side of the apparatus.

A. Naive male DBA2 mice (25-30) were housed on a reversed light/dark cycle and tested during the dark phase of the cycle under dim red light. The apparatus consisted of an open topped box (40 cm long × 27 cm wide × 27 cm high) divided into a small area (2/5) and a large area (3/5) by a partition that extended 20 cm above the walls. There was a 7.5 × 7.5 cm opening in the partition at floor level. The small compartment was painted black and the large compartment white. The floor of each compartment was marked into 9 cm squares. The white compartment was illuminated by a 100 W tungsten bulb 17 cm above the box and the black compartment by a similarly placed 60 W red bulb.

Animals that had been injected with drug or vehicle were placed individually into the center of the white area and their behavior observed during a 5 minute period by remote video recording. Four behavioral parameters were recorded every minute: the number of exploratory rears in the white and black sections, the number of line crossings in the black and white sections, the number of transitions between the two sections and the time spent in the black and white sections. Animals were tested in treatment groups of 8-10 and vehicle controls were run on each test day. Data were analysed by ANOVA and Dunnetts test.

In one series of tests, the following compounds were employed:

Compound A: 3(S)-(-)-1,3-dihydro-3-(2-indolecarbonylamino)-1-methyl-5-phenyl-2H-1,4-benzodiazepin-2-one, an effective antagonist of CCK-A receptors;

Compound B: (R)-N-(2,3-dihydro-1-methyl-2-oxo-5-phenyl-1H-1,4-benzodiazepin-3-yl)-N'-(3-methylphenyl)urea, an effective antagonist of CCK-B receptors.

Vehicle treated animals displayed a marked preference for activity in the black side of the test arena, probably induced by the aversive properties of the brightly lit, white painted section. Compound A at doses of 0.05, 0.5, 5.0 and 500 ug/kg significantly decreased the preference for rearing in the black side. Similarly, 0.5, 5.0 and 500 ug/kg of Compound A abolished the preference for locomotion (line crossings) in the black side. The difference in time spent in the black and white side was abolished by 5.0 and 500 ug/kg of Compound A. Compound B at a dose of 0.05 ug/kg abolished the preference for rearing in the black side and a dose of 0.005 ug/kg decreased the difference in time spent in the black and white side.

These results demonstrate that CCK antagonists have anxiolytic properties in mice. The active dose range for Compound B (0.005-0.05 ug/kg) was lower than that for Compound A (0.05-5.0 ug/kg), suggesting that the response may be mediated by CCK-B receptors. This is consistent with studies in humans in which CCK-4 (which is a preferential CCK-B receptor agonist) was reported to induce panic, whereas CCK-8 (which is equipotent as an agonist at CCK-A and CCK-B receptors) induced gastrointestinal effects but not panic symptoms. Therefore, compounds A and B are clinically useful in the treatment of anxiety.

B. The effects of CCK-8 and compound A on the exploratory behavior of the rat were examined in automated activity cages and by direct observation. It is know that exogenous CCK-8 decreases exploratory behavior in rats in a novel environment by accelerating the process of habituation. [See Crawley, Pharm. Biochem & Behav. 20, 23-27 (1984).]

Expt 1

Male Sprague Dawley rats were injected (i.p.) with CCK-8 and immediately placed in automated activity cages. Activity was measured for 30 minutes past injection. CCK-8 (0.5-16 μg/kg) dose-dependently decreased locomotor activity $F(6,87)=3.21$ ($p<0.01$). These results confirm previous reports that CCK decreases locomotor activity in a novel environment.

Expt 2

Male SD rats were injected (s.c.) with the CCK antagonist compound A (0.0001-10 mg/kg) and immediately placed in the automated activity cages. Compound A delayed habituation and prolonged the period of exploratory activity of the rats $F(6,124)=2.54$, $p<0.05$. The drug effects were most pronounced at 25 minutes where 0.1 mg/kg induced levels of activity significantly above controls $F(6.124)=3.18$, $p<0.01$. The dose response curve was bell-shaped with higher and lower doses having no significant effect on activity at the time point. As the anxiolytic drug chlordiazepoxide also increases spontaneous locomotor activity in rats in a novel environment [(McElroy et al. *Psychopharm.* 85: 224–226 (1985)] these findings are consistent with an anxiolytic action of Compound A useful in the treatment of panic disorder.

Expt 3

In order to assess further the effect of Compound A on exploration in a novel environment, the motoric behaviors of rats placed in a perspex cage was recorded by direct observation for a 15 minute period 15 minutes after treatment with Compound A.

Experimenters (unaware of the treatments the animals had received) recorded the frequency and duration of rearing, sniffing, grooming and cage crossing using a keypad interfaced to a BBC microcomputer.

Sniffing, ($F(3,43)=3.96$, $P<0.01$) rearing ($F(3,43)=4.77$, $P<0.01$) and cage crossing ($F(3,43)=3.79$, $P<0.05$) were all significantly increased by 0.1 mg/kg of Compound A. These results are consistent with the data from the automatic activity measures (see Experiment 2) and further support the utility of compound A in the treatment of panic disorder.

2. CCK Receptor Binding (Pancreas)

CCK-33 was radiolabeled with $^{125}$I-Bolton Hunter reagent (2000 Ci/mmole) as described by Sankara et al. (J. Biol. Chem. 254: 9349–9351, 1979). Receptor binding was performed according to Innis and Snyder (Proc. Natl. Acad. Sci. 77, 6917–6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200–350 g) were sacrificed by decapitation. The whole pancreas was dissected free of fat tissue and was homogenized in 20 volumes of ice-cold 50 mM Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33.

3. CCK Receptor Binding (Brain)

CCK-33 was radiolabeled and the binding was performed according to the description for the pancreas method with modifications according to Saito et al., J. Neurochem. 37:483–490, 1981.

Male Hartley guinea pigs (300–500 g) were sacrificed by decapitation and the brains were removed and placed in ice-cold 50 mM Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 minutes. Pellets were resuspended in Tris Buffer, centrifuged as above and resuspended in 200 volumes of binding assay buffer (10 mM N-2-hydroxyethyl-piperazine-N'-2-ethane sulfonic acid (HEPES), 5 mM $MgCl_2$, 0.25 mg/ml bacitracin, 1 mM ethylene glycol-bis-(β-aminoethylether-N,N'-tetraacetic acid) (EGTA), and 0.4% bovine serum albumin (BSA)). For the binding assay, 25 μl of buffer (for total binding) or unlabeled CCK-8 sulfate to give a final concentration of 1 μm (for nonspecific binding) or the compounds of this invention (for determination of inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of this invention can be determined to be competitive antagonists of CCK according to the following assays.

4. Isolated Guinea Pig Gall Bladder

Male Hartley guinea pigs (400–600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, $KH_2PO_4$ 1.19 mM, Mg $So_4$ 1.2 mM, $NaHCO_3$ 25 mM and dextrose 11 mM) maintained at 32° C. and bubbled with 95% $O_2$ and 5% $CO_2$. Isometric contractions are recorded using Statham (60 g; 0.12 mm) strain gauges and a Hewlett-Packard (77588) recorder. The tissues are washed every 10 minutes for 1 hour to obtain equilibrium prior to the beginning of the study. CCK-8 is added cumulatively to the baths and $EC_{50}$'s determined using regression analysis. After washout (every 10 minutes for 1 hour), the compounds of this invention are added at least 5 minutes before the addition of CCK-8 and the $EC_{50}$ of CCK-8 in the presence of the compounds of this invention similarly determined.

Isolated Longitudinal Muscle of Guinea Pig Ileum

Longitudinal muscle strips with attached nerve plexus are prepared as described in *Brit. J. Pharmac.* 23:; 356–363, 1964; *J. Physiol.* 194: 13–33, 1969. Male Hartley guinea pigs are decapitated and the ileum removed (10 cm of the terminal ileum is discarded and the adjacent 20 cm piece used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds of this invention determined as described in the gall bladder protocol (above).

6. Gastrin Antagonism

Gastrin antagonist activity of compounds of this invention is determined using the following assay.

A. Gastrin Receptor Binding in Guinea Pig Gastric Glands

Preparation of guinea pig gastric mucosal glands

Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300–500 g body weight, male Hartley) were washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

B. Binding Studies

The washed guinea pig gastric glands prepared as above were resuspended in 25 ml of standard buffer containing 0.25 mg/ml of bacitracin. For binding studies, to 220 μl of gastric glands in triplicate tubes, 10 μl of buffer (for total binding) or gastrin (1 μM final concentration, for nonspecific binding) or test compound and 10 μl of $^{125}I$-gastrin (NEN, 2200 Ci/mmole, 25 pM final) or $^3H$-pentagastrin (NEN 22 Ci/mmole, 1 nM final) were added. The tubes were aerated with 95% $O_2$ and 5% $CO_2$ and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}I$-gastrin or liquid scintillation counting for $^3H$-pentagastrin.

In Vitro Results

Effect of the compounds of this invention on $^{125}I$-CCK-33 receptor binding

The preferred compounds of this invention are those which inhibited specific $^{125}I$-CCK-33 binding in a concentration dependent manner.

Scatchard analysis of specific $^{125}I$-CCK-33 receptor binding in the absence and presence of the compounds of this invention indicated the compounds competitively inhibited specific $^{125}I$-CCK-33 receptor binding since it increased the $K_D$ (dissociation constant) without affecting the $B_{max}$ (maximum receptor number). A $K_i$ value (dissociation constant of inhibitor) of the compounds of this invention was estimated.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of 1-Methyl-2-(2'indolecarbonyl)aminomethyl-5-(2'-fluorophenyl)-2,3-dihydro-1H-1,4,-benzodiazepine

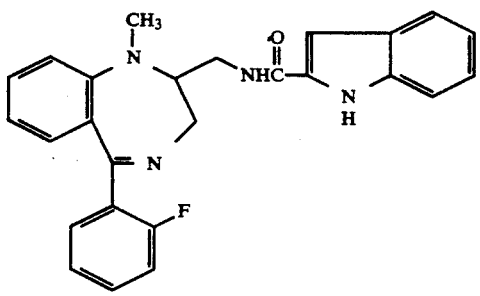

1-Methyl-2-aminomethyl-5-(2'-fluorophenyl)-2,3-dihydro-1H-1,4-benzodiazepine (250 mg, 0.88 mmole) and 2-indole carboxylic acid (142 mg, 0.88 mmole) were combined with 5 ml of dry methylene chloride, and 1-ethyl-3-(3-dimethylaminopropyl)carbodiimide hydrochloride (169 mg, 0.88 mmole) was added to this mixture at room temperature. The pH of the reaction mixture was adjusted to 8.5 with triethylamine and after overnight stirring, the reaction mixture was diluted with ethyl acetate (200 ml) and the organic phase was washed with saturated sodium bicarbonate solution and brine. Rotoevaporation of the dried ($MgSO_4$) extracts afforded 300 mg of an oil which was purified by silica gel chromatography (ethyl acetate-hexane elution, 2:1 v/v) to give the analytical sample (150 mg) which was 99% pure by HPLC.

MS (70 ev): 426 (M+), 253,255,144.

Pmr ($CDCl_3$): according to theory.

Elemental Analysis: $C_{26}H_{23}FN_4O$ $0.2H_2O$: Calc: N, 13.02, C, 72.60; H, 5.48. Found: N, 12.41; C, 72.75; H, 5.43.

EXAMPLE 2

Preparation of 1-methyl-2-(4-thianaphthenemethylcarbonyl-(aminomethyl-5-(2'-fluorophenyl)-2,3-dihydro-1H-1,4-benzodiazepine

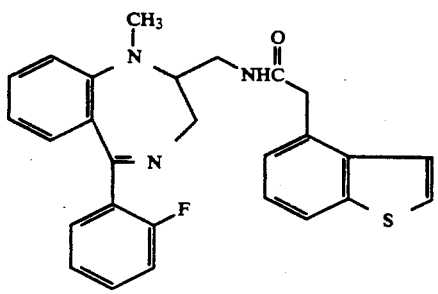

According to the method of Example 1 1-methyl-2-aminomethyl-5-(2'-fluorophenyl)-2,3-dihydro-1H-1,4- benzodiazepine (250 mg, 0.88 mmole) and 4-thianaphthene acetic acid (170 mg, 0.88 mmole) were combined with 4 ml of dry methylene chloride, and 1-ethyl-3-(3-dimethylaminopropyl)carbodiimide hydrochloride (169 mg, 0.88 mmole) was added to this mixture. After pH adjustment, overnight stirring, dilution and washing, rotoevaporation of the dried extracts of the reaction afforded 300 mg of an oil which was purified by silica gel chromatography (ethyl acetate-hexane elution, 4:1 v/v) to give the analytical sample (100 mg) which was 88% pure by HPLC.

MS (FAB): 458 (M++H), 253,147.

Pmr (CDCl$_3$): according to theory.

Elemental Analysis: C$_{27}$H$_{24}$FN$_3$OS 0.2H$_2$: N, 9.11, C, 70.31; H, 5.33. Found: N, 8.82; C, 70.27; H, 5.27.

EXAMPLE 3

Preparation of
1-methyl-2-(2-L-hydroxy-2-phenylacetyl)aminomethyl-5-(2'-fluorophenyl)-2,3-dihydro-1H-1,4-benzodiazepine

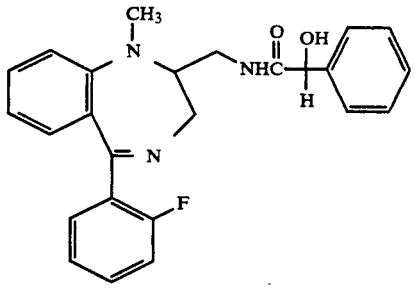

According to the method of Example 1, 1-methyl-2-aminomethyl-5-(2'-fluorophenyl)-2,3-dihydro-1H-1,4-benzodiazepine (500 mg, 1.76 mmole) and L-mandelic acid (268 mg, 1.76 mmole) were combined with 5 ml of dry methylene chloride, and 1-ethyl-3-(3-dimethylaminopropyl)carbodiimide hydrochloride (337 mg, 1.76 mmole) was added to this mixture. After pH adjustment, overnight stirring, dilution (with 250 ml of ethyl acetate) and washing, rotoevaporation of the dried extracts of the reaction afforded 540 mg of an oil which was purified by silica gel chromatography (chloroform-ethanol ammonia elution, 95:5:0.05 v/v) to give the analytical sample which was 94% pure HPLC.

MS (20 ev): 417 (M+), 310,253,225.

Pmr (CDCl$_3$): according to theory.

Elemental Analysis: C$_{25}$H$_{24}$FN$_3$O$_2$ 0.2H$_2$O: N, 9.98, C, 71.30; H, 5.84. Found: N, 9.80; C, 71.31; H, 5.93.

EXAMPLE 4

Preparation of
1-methyl-2-(1H-indol-3-yl)methylcarbonylamino-yl-5-(2'-fluorophenyl)-2,3-dihydro-1H-1,4-benzodiazepine hydrate

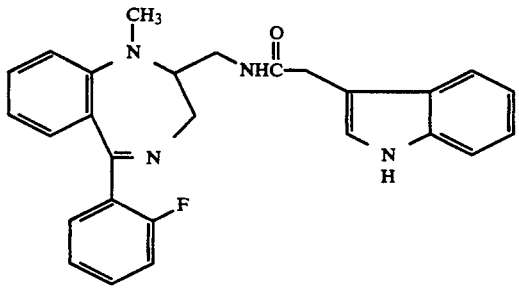

According to the method of Example 1, 1-methyl-2-aminomethyl-5-(2'-fluorophenyl)-2,3-dihydro-1H-1,4-benzodiazepine (250 mg, 0.88 mmole) and indole-3-acetic acid (154 mg, 0.88 mmole) were combined with 4 ml of dry methylene chloride, and 1-ethyl-3-(3-dimethylaminopropyl)carbodiimide hydrochloride (169 mg, 0.88 mmole) was added to this mixture. After pH adjustment, overnight stirring, dilution and washing, rotoevaporation of the dried extracts of the reaction afforded 290 mg of an oil which was purified by silica gel chromatography (ethyl acetate elution) to give material which was 70% pure by HPLC. Rechromatography (chloroformethanol elution, 95:5 v/v) afforded the analytical sample, 93% pure, as a yellow solid.

MS (20 ev): 440 (M+), 253,225,130.

Pmr (CDCl$_3$): according to theory.

Elemental Analysis: C$_{27}$H$_{25}$FN$_4$O H$_2$O: Calc: N, 12.22, C, 70.72; H, 5.93. Found: N, 12.23; C, 70.89; H, 5.62.

EXAMPLE 5

Preparation of
1-methyl-2-[1-(S)-methoxycarbonyl-2-phenylethylamino]methyl-5-(2'-fluorophenyl)-2,3-dihydro-1H-1,4-benzodiazepine

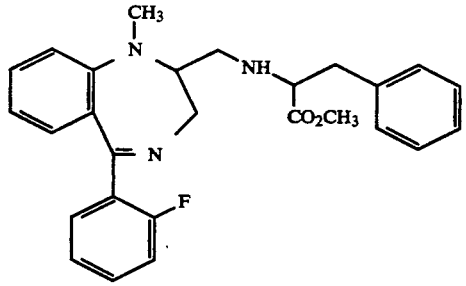

1-Methyl-2-chloromethyl-5-(2'-fluorophenyl)-2,3-dihydro-1H-1,4-benzodiazepine (150 mg, 0.5 mmole) and methyl-2(S)-amino-3-phenylpropionate (108 mg, 0.5 mmole) were combined in 4 ml of dry N,N-dimethylformamide, and potassium carbonate (138 mg, 1 mmole) and sodium iodide (70 mg, 0.5 mmole) were added to this mixture. The reaction mixture was protected from moisture and heated at 60° C. for 48 hours. The solvent was then removed under reduced pressure and the residue was partitioned between ethyl acetate (100 ml) and saturated sodium bicarbonate solution (50 ml). The phases were separated and the organic layer was washed with sodium bicarbonate solution and brine, then dried (MgSO₄) and concentrated to yield 300 mg of crude product. The analytical product was obtained via chromatography on silica gel (ethyl acetate-hexane elution, 7:3 v/v) as a mixture of diasteriomers; 95% pure by HPLC.

MS (20 ev): 445 (M+), 253,225,212,83.

Pmr (CDCl₃): according to theory.

Elemental Analysis: $C_{27}H_{28}FN_3O_2 \cdot 0.6H_2O$: Calc: N, 9.20, C, 71.05; H, 6.45. Found: N, 8.81; C, 71.01; H, 6.56.

EXAMPLE 6

Preparation of 1-methyl-2-(3'-trifluoromethylphenyl)aminomethyl-5-(2'-fluorophenyl)-2,3-dihydro-1H-1,4-benzodiazepine

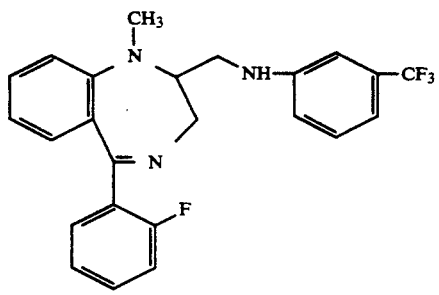

According to the method of Example 5, 1-methyl-2-chloromethyl-5-(2'-fluorophenyl)-2,3-dihydro-1H-1,4-benzodiazepine (200 mg, 0.66 mmole) and m-trifluoromethyl aniline (319 mg, 1.97 mmole) were combined in 2 ml of dry N,N-dimethylformamide, and potassium carbonate (273 mg, 1.97 mmole) and sodium iodide (198 mg, 1.32 mmole) were added to this mixture (which was heated at 65° C. for 18 hours). After solvent-removal, partitioning, separation, washing, drying and concentrating, the analytical product was obtained via chromatography on silica gel (ethyl acetate-hexane elution, 3:7 v/v) and was shown to be 96% pure by HPLC.

MS (30 ev): 427 (M+), 253,225,117,83.

Pmr (CDCl₃): according to theory.

Elemental Analysis: $C_{24}H_{21}F_4N_3 \cdot 0.1H_2O$: Calc: N, 9.79 C, 67.15; H, 4.97. Found: N, 9.86; C, 66.99; H, 5.09.

EXAMPLE 7

Preparation of 1-methyl-2-[2-((1,1-dimethylethoxy)carbonyl)amino-3-(1H-indol-3-yl)propanoyl]aminomethyl-5-(2'-fluorophenyl)-2,3-dihydro-1H-1,4-benzodiazepine

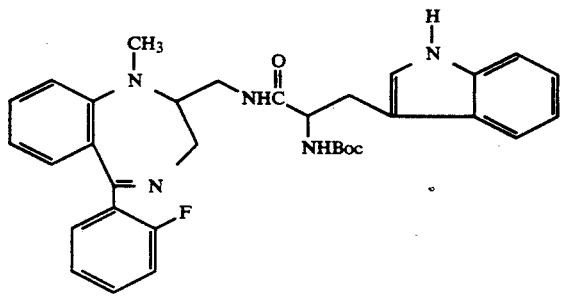

According to the method of Example 1, 1-methyl-2-aminomethyl-5-(2'-fluorophenyl)-2,3-dihydro-1H-1,4-benzodiazepine (250 mg, 0.88 mmole) and L-2-((1,1-dimethylethoxy)carbonyl)amino-3-(1H-indol-3-yl)propanoic acid (269 mg, 0.88 mmole) were combined with 4 ml of dry methylene chloride, and 1-ethyl-3-(3-dimethylaminopropyl)carbodiimide hydrochloride (169 mg, 0.88 mmole) was added to this mixture. After pH-adjustment, overnight stirring, dilution and washing, rotoevaporation of the dried extracts of the reaction afforded 500 mg of a foam which was purified by silica gel chromatography(chloroform-ethanol-ammonia elution, 90:10:1 v/v) to give the analytical sample (270 mg) which was 98% pure by HPLC; m.p. 124° C.

MS (FAB): 570 (M+ +H), 514,253.

Pmr (CDCl₃): according to theory.

Elemental Analysis: $C_{33}H_{36}FN_5O_3 \cdot 0.3H_2O$: N, 12.17; C, 68.91; H, 6.42. Found: N, 12.15; C, 68.91; H, 6.71.

EXAMPLE 8

Preparation of 1-methyl-2-[(2-methylpropoxy)carbonyl]-amino-methyl-5-(2'-fluorophenyl)-2,3-dihydro-1H-1,4-benzodiazepine

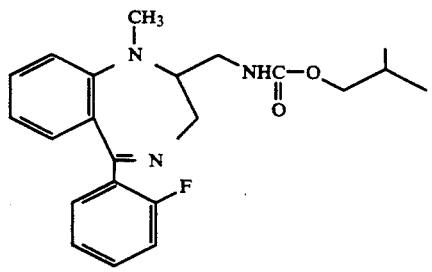

According to the method of Example 1, 1-methyl-2-aminomethyl-5-(2'-fluorophenyl)-2,3-dihydro-1H-1,4-benzodiazepine (250 mg, 0.88 mmole) and isobutyl chloroformate (114 μl, 0.88 mmole) were combined with 4 ml of dry methylene chloride, and 97 μl of N-methylmorpholine (0.88 mmole) at −5° C. was added to the mixture. The resulting reaction mixture was allowed to warm to room temperature over 2 hours, and after dilution and washing, rotoevaporation of the dried extracts of the reaction afforded 230 mg of an oil which was purified by silica gel chromatography (ethyl acetate-hexane elution, 7:3 v/v) to give the analytical sample (120 mg) which was 98% pure by HPLC.

MS (20 ev): 398 (M+), 383,281,253,225.

Pmr (CDCl₃): according to theory.

Elemental Analysis: $C_{22}H_{26}FN_3O_2 \cdot 0.6H_2O$: N, 10.65; C, 67.02; H, 6.95. Found: N, 10.65; C, 66.92; H, 6.90.

EXAMPLE 9

Preparation of
1-Methyl-2-[2-amino-3-(1H-indol-3-yl)-propanoyl-]aminomethyl-5-(2'-fluorophenyl)-2,3-dihydro-1H-1,4-benzodiazepine dihydrochloride sesquihydrate

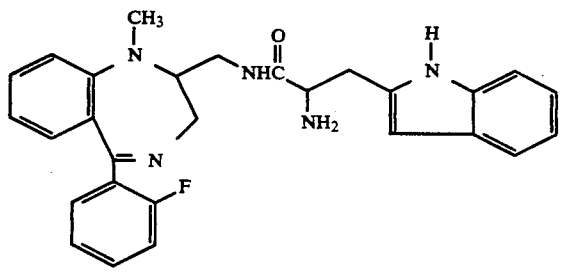

1-Methyl-2-[2-((1,1-dimethylethoxy)carbonyl)amino-3-(1H-indol-3-yl)propanoyl]aminomethyl-5-(1'-fluorophenyl)-2,3-dihydro-1H-1,4-benzodiazepine (50 mg, 0.08 mmole) was dissolved in 2 ml of ethyl acetate, cooled to 0° C. and treated with hydrogen chloride gas for 1 hour. The solvent and excess hydrogen chloride were removed under reduced pressure to give the product as a foam which was 96% pure by HPLC.

MS (FAB): 470 (M+ +H), 185.
Pmr (CD$_3$OD): according to theory.
Elemental Analysis: C$_{28}$H$_{30}$Cl$_2$FN$_5$1.5H$_2$O: N, 12.30; C, 59.04; H, 5.79. Found: N, 11.67; C, 59.23; H, 5.89.

EXAMPLE 10

Preparation of
1-Methyl-2-(2-methoxy-2-trifluoromethyl-2-phenylacetyl)aminomethyl-5-(2'-fluorophenyl)-2,3-dihydro-1H-1,4-benzodiazepine

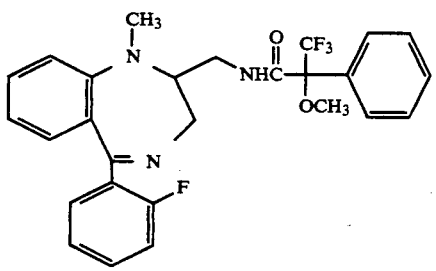

According to the method of Example 1, 1-methyl-2-aminomethyl-5-(2'-fluorophenyl)dihydro-1H-1,4-benzodiazepine (250 mg, 0.88 mmole) and (−)-L-methoxy-L-(trifluoromethyl)phenylacetice acid (222 mg, 0.95 mmole) were combined with 4 ml of dry methylene chloride, and 1-ethyl-3-(3-dimethylaminopropyl)carbodiimide hydrochloride (182 mg, 0.95 mmole) was added to the mixture. After pH adjustment, overnight stirring, dilution and washing, rotoevaporation of the dried extracts afforded 400 mg of a solid, as a mixture of diastereomers, which was purified by silica gel chromatography (ethyl acetatehexane elution, 2:3 v/v) to give the analytical sample (200 mg) which was pure by HPLC.

MS (20 ev): 499 (M+), 253,225,189.
Pmr (CDCl$_3$): according to theory.
Elemental Analysis: C$_{27}$H$_{25}$F$_4$N$_3$0.75H$_2$O: N, 8.19; C, 63.21; H, 5.20. Found: N, 8.08; C, 63.12; H, 4.99.

EXAMPLE 11

Preparation of
1-Methyl-2-[2(S)-((1,1-dimethylethoxy)-carbonyl)amino-3-acetamidomethylmercaptopropanoyl]-aminomethyl-5-(2'-fluorophenyl)-2,3-dihydro-1H-1,4-benzodiazepine hemihydrate

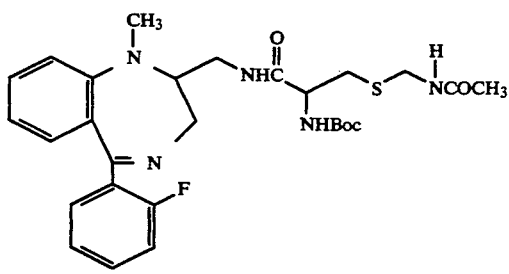

According to the method of Example 1, 1-methyl-2-aminomethyl-5-(2'-fluorophenyl)-2,3-dihydro-1H-1,4-benzodiazepine (620 mg, 2.18 mmole) and 2(S)-((1,1-dimethylethoxy)carbonyl)amino-3-acetamidomethyl-mercaptopropanoic acid (643 mg, 2.20 mmole) were combined with 10 ml of dry methylene chloride, and 1-ethyl-3-(3-dimethylaminopropyl)-carbodiimide hydrochloride (422 mg, 2.20 mmole) was added to the mixture. After pH adjustment, overnight stirring, dilution and washing, rotoevaporation of the dried extracts afforded 1 g of crude product which was purified by silica gel chromatography (chloroform-ethanol elution, 94:6 v/v) to give the analytical sample (420 mg) which was 96% pure by HPLC, mp 100°-103° C.

MS (FAB): 558 (M+ +H).
Pmr (CDCl$_3$): according to theory.
Elemental Analysis: C$_{28}$H$_{36}$FN$_5$0.5H$_2$O: N, 12.36; C, 59.34; H, 6.58. Found: N, 12.47; C, 59.14; H, 6.66.

EXAMPLE 12

Preparation of
1-Methyl-2-benzoylsuccinoylaminomethyl-5-(2'-fluorophenyl)-2,3-dihydro-1H-1,4-benzodiazepine

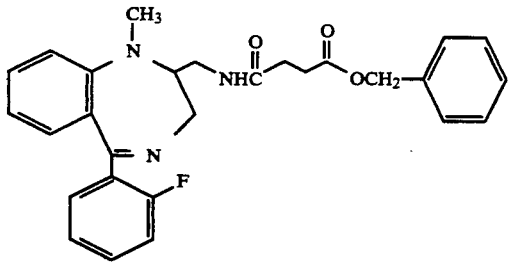

According to the method of Example 1, 1-methyl-2-aminomethyl-5-(2'-fluorophenyl)-2,3-dihydro-1H-1,4-benzodiazepine 9250 mg, 0.88 mmole) and benzylsuccinic acid 9185 mg, 0.88 mmole) were combined with 5 ml of dry methylene chloride, and 1-ethyl-3-(3-dimethylaminopropyl)carbodiimide hydrochloride (169 mg, 0.88 mmole) was added to the mixture. After pH adjustment, overnight stirring, dilution and washing, rotoevaporation of the dried extracts afforded 360 mg of an oil which was purified by silica gel chromatography (chloroform-ethanol elution, 95:5 v/v) to give the analytical sample (140 mg) which was 88% pure by HPLC.

MS (20 ev): 473 (M+), 365,253,238,225,108.

Pmr (CDCl₃): according to theory.
Elemental Analysis: $C_{28}H_{28}FN_3O_3 \cdot 0.3H_2O$: N, 8.77; C, 70.21; H, 6.01. Found: N, 8.93; C, 70.35; H, 6.08.

EXAMPLE 13

Preparation of 1-Methyl-2-(acetamidomethylmercaptoacetyl-)aminomethyl-5-(2'-fluorophenyl)-2,3-dihydro-1H-1,4-benzodiazepine hydrate

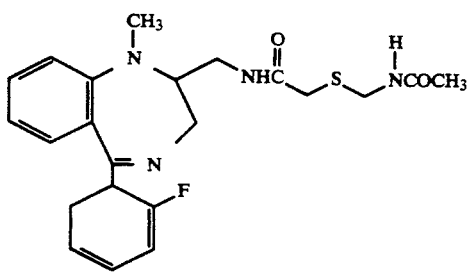

According to the method of Example 1, 1-methyl-2-aminomethyl-5-(2'-fluorophenyl)-2,3-dihydro-1H-1,4-benzodiazepine (250 mg, 0.88 mmole) and benzylsuccinic acid (185 mg, 0.88 mmole) were combined with 5 ml of dry methylene chloride, and 1-ethyl-3-(3-dimethylaminopropyl)carbodiimide hydrochloride (169 mg, 0.88 mmole) was added to the mixture. After pH adjustment, overnight stirring, dilution with 250 ml of ethyl acetate and washing, rotoevaporation of the dried extracts afforded 2.63 g of an oil which was purified by silica gel chromatography (chloroform-ethanol-ammonia elution, 90:10:1 v/v) to give the analytical sample (850 mg) which was 95% pure by HPLC.

MS (30 ev): 428 (M+), 253,225.
Pmr (CDCl₃): according to theory.
Elemental Analysis: $C_{22}H_{25}FN_4O_2S \cdot H_2O$: N, 12.54; C, 59.17; H, 6.09. Found: N, 12.68; C, 59.37; H, 5.89.

What is claimed is:

1. A method of treating panic disorder or anxiety disorder in a mammal which comprises administering to said mammal a therapeutically effective amount of a compound of formula I:

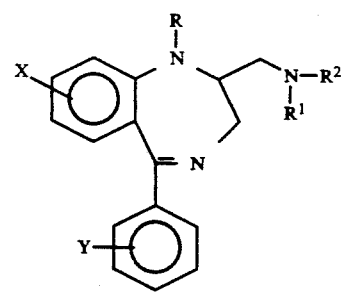

wherein:
X is one or two of the substituents: F, Cl or Br; $C_1$–$C_4$-straight- or branched-chain alkyl, including methyl, ethyl, propyl, isopropyl, butyl, isobutyl, and t-butyl; $C_1$–$C_4$-alkoxy; $C_1$–$C_4$-alkylthio; hydroxy; nitro; cyano; amino; or trifluoromethyl, and may be attached at either or both the 7- and/or 8-positions;

Y is independently, the same as X, and may be attached at any of positions 2–6 on the aromatic ring;

R is H, $C_1$–$C_4$-alkyl, cyclo-$C_3$–$C_5$-alkyl, $C_1$–$C_4$-alkenyl, or acetyl;

$R^1$ is H, $C_1$–$C_4$-alkyl, or cyclo-$C_3$–$C_5$-alkyl;

$R^2$ is unsubstituted or mono- or disubstituted phenyl, where the substituents are as defined under X, above;

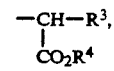

where $R^3$ is $(CH_2)_n$-$C_1$–$C_4$-alkyl, —$(CH_2)_n$-2-indole, —$(CH_2)_n$-3-indole, or —$(CH_2)_n$-phenyl (unsubstituted or mono- or disubstituted, where the substituents are as defined for X, above), where n is 0–4, and $R^4$ is H or $C_1$–$C_4$-alkyl;

where $R^5$ is

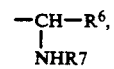

wherein $R^6$ is $(CH_2)_n$-2-indole, or $(CH_2)_n$-3-indole, where n is 0–4, where $R^7$ is H, $COOR^8$, or

and where $R^8$ is $C_1$–$C_4$-alkyl; where $R^5$ is $(CH_2)_mSCH_2NHCOCH_3$, where m is 1–4; where $R^5$ is $C_1$–$C_4$-alkyl; where $R^5$ is pyrazine (unsubtituted or mono-substituted where the substituents may be Cl, $COOR^8$, CN or $NO_2$), wherein $R^8$ is as defined above;

where $R^5$ is

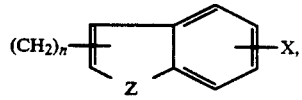

wherein Z is O, S or NR, $(CH_2)_n$ is attached at the 2- or 3-position, and R, n and x are as defined above;

where $R^5$ is

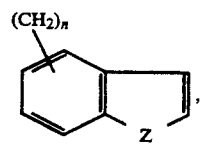

wherein $(CH_2)_n$ is attached at the 4- or 5-position, and n and Z are as defined above; where $R^5$ is $(CH_2)_mCO_2CH_2phenyl$, wherein m is as defined above;

where $R^5$ is —O—$C_1$–$C_4$-alkyl, —$CHOHC_6H_5$, or

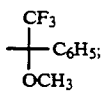

or of the formula II:

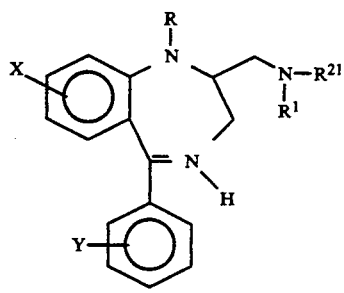

wherein:

X, Y, R and R¹ are as defined above; and R²¹ is R² as defined above, including wherein R⁵, as defined above, also is pyridine,

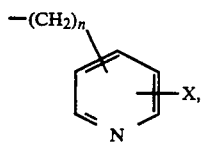

where $(CH_2)_n$ is attached at the 2-, 3- or 4-position and n and X are as defined above;

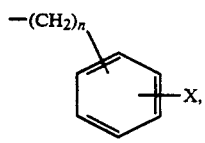

where the point of attachment is at any position on the ring and n and X are as defined above; or

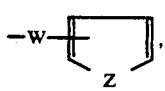

where the point of attachment is at the 2- or 3-position and W is H, straight or branched chain $C_1$–$C_4$-alkyl or $C_1$–$C_4$-alkoxy, nitro, F, Cl or Br, and Z is as defined above; or the optical isomers of formula I, or pharmaceutically acceptable salts of the compounds of formulas I or II.

2. A method of directly inducing analgesia, anesthesia or loss of sensation of pain in a mammal which comprises administering to an animal requiring such treatment therapeutically effective amount of a compound of formula I:

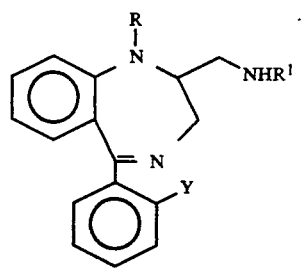

wherein:

X is one or two of the substituents: F, Cl or Br; $C_1$–$C_4$-straight- or branched-chain alkyl, including methyl, ethyl, propyl, isopropyl, butyl, isobutyl, and t-butyl; $C_1$–$C_4$-alkoxy; $C_1$–$C_4$-alkylthio; hydroxy; nitro; cyano; amino; or trifluoromethyl, and may be attached at either or both the 7- and/or 8-positions;

Y is independently, the same as X, and may be attached at any of positions 2–6 on the aromatic ring;

R is H, $C_1$–$C_4$-alkyl, cyclo-$C_3$–$C_5$-alkyl, $C_1$–$C_4$-alkenyl, or acetyl;

R¹ is H, $C_1$–$C_4$-alkyl, or cyclo-$C_3$–$C_5$-alkyl;

R² is unsubstituted or mono- or disubstituted phenyl, where the substituents are as defined under X, above;

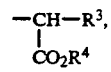

where R³ is $(CH_2)_n$-$C_1$–$C_4$-alkyl, —$(CH_2)_n$-2-indole, —$(CH_2)_n$-3-indole, or —$(CH_2)_n$-phenyl (unsubstituted or mono- or disubstituted, where the substituents are as defined for X, above), where n is 0–4, and R⁴ is H or $C_1$–$C_4$-alkyl;

where R⁵ is

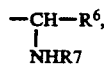

wherein R⁶ is $(CH_2)_n$-2-indole, or $(CH_2)_n$-3-indole, where n is 0–4, where R⁷ is H, COOR⁸, or

and where R⁸ is $C_1$–$C_4$-alkyl;

where R⁵ is $(CH_2)_mSCH_2NHCOCH_3$, where m is 1–4; where R⁵ is $C_1$–$C_4$-alkyl; where R⁵ is pyrazine (unsubstituted or mono-substituted where the substituents may be Cl, COOR⁸, CN or $NO_2$), wherein R⁸ is as defined above;

where R⁵ is

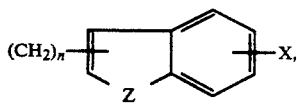

wherein Z is O, S or NR, $(CH_2)_n$ is attached at the 2- or 3-position, and R, n and X are as defined above;
where $R^5$ is

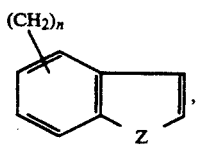

wherein $(CH_2)_n$ is attached at the 4- or 5-position, and n and Z are as defined above; where $R^5$ is $(CH_2)_mCO_2CH_2$phenyl, wherein m is as defined above;
where $R^5$ is —O—$C_1$-$C_4$-alkyl, —CHOHC$_6$H$_5$, or $R^5$ is

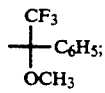

or of the formula II:

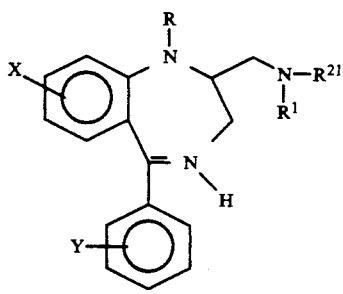

wherein:

X, Y, R and $R^1$ are as defined above; and $R^{21}$ is $R^2$ as defined above, including wherein $R^5$, as defined above, also is pyridine,

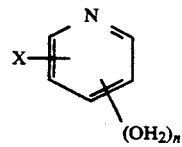

where $(CH_2)_n$ is attached at the 2-, 3-or 4-position and n and X are as defined above;

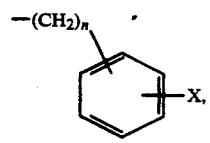

where the point of attachment is at any position on the ring and n and X are as defined above; or

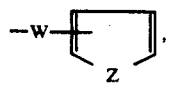

where the point of attachment is at the 2- or 3-position and W is H, straight or branched chain $C_1$-$C_4$-alkyl or $C_1$-$C_4$-alkoxy, nitro, F, Cl or Br, and Z is as defined above; or
the optical isomers of formula I, or pharmaceutically acceptable salts of the compounds of formulas I or II.

3. The method according to claim 1, wherein the therapeutically effective amount of the compound of formula I is from about 0.005 mg/kg to about 50 mg/kg of body weight, administered to said mammal in a single or divided dose.

4. The method according to claim 2, wherein the therapeutically effective amount of the compound of formula I is from about 0.005 mg/kg to about 50 mg/kg of body weight, administered to said mammal in a single or divided dose.

5. The method according to claim 1, wherein said mammal is a human.

6. The method according to claim 2, wherein said mammal is a human.

* * * * *